United States Patent [19]

Hayes

[11] 4,452,805

[45] Jun. 5, 1984

[54] FUNGICIDAL MIXTURES COMPRISING AN IMIDAZOLE AND AN AMINE

[75] Inventor: Edward S. S. Hayes, Holgate, Australia

[73] Assignee: FBC Limited, Hauxton, England

[21] Appl. No.: 397,965

[22] Filed: Jul. 14, 1982

[30] Foreign Application Priority Data

Jul. 14, 1981 [GB] United Kingdom ............... 8121578

[51] Int. Cl.$^3$ ............................................. A01N 43/50
[52] U.S. Cl. ................................................ 424/273 R
[58] Field of Search ................................... 424/273 R

[56] References Cited

PUBLICATIONS

Takahi et al.; C.A. vol. 84 (1976), 26864u.
Birchmore et al.; C.A. vol. 89 (1978), 210275g.

Primary Examiner—Allen J. Robinson
Attorney, Agent, or Firm—Lawrence Rosen

[57] ABSTRACT

The fungicidal activity of prochloraz, particularly against organisms which cause storage rot of fruit, is enhanced by the addition of guazatine.

2 Claims, No Drawings

FUNGICIDAL MIXTURES COMPRISING AN IMIDAZOLE AND AN AMINE

This invention relates to compositions with useful fungicidal properties.

The present invention provides a fungicidal composition comprising prochloraz and guazatine.

Prochloraz is a known fungicide and is the approved common name for 1-[N-propyl-N-2-(2,4,6-trichlorophenoxy) ethylcarbamoyl]imidazole, and that name is used in the specification to also include salts and metal complexes of this compound. Guazatine is the approved common name for bis(8-guanadinooctyl)amine and that name is used in the specification to also include salts.

We have found that the compositions of the invention have advantageous properties over the individual components and that synergism is often demonstrated.

The ratios of the prochloraz to the guazatine vary over a wide range but are usually in the range 5:1 to 1:5 e.g. 2:1 to 1:2 and particularly in a 1.5:1 ratio. These ratios are based on the weights of the free bases.

In addition other pesticides may be employed in conjunction with the active ingredients described above providing they do not adversely affect the interaction between the fungicidal components. For example it is sometimes useful to include additional fungicides which extend the range of activity in order to control a wider spectrum of fungi.

The compositions of the invention are especially useful for the control of fungi which cause fruit storage rot e.g. Penicillium spp, *Geotrichum candidum, Aspergillus spp*, and Botrytis spp. They are also useful in controlling a wide range of other fungi e.g. powdery mildew (*Erysiphe graminis*) on cereal crops such as wheat, barley, oats and rye and other foliar diseases such as glume blotch (*Septoria nodorum*), leaf blotch (*Rhynchosporium secalis*), eyespot (*Pseudocercosporella herpotrichoides*) and rust (e.g. *Puccinia graminis*). Certain compositions of the present invention can be used to control seed borne organisms such as bunt (*Tilletia caries*) on wheat, loose smut (*Ustilago nuda* and *Ustilago hordei*) on barley and oats, leaf spot (*Pyrenophora avenae*) on oats and leaf stripe (*Pyrenophora graminis*) on barley. The compositions can also be applied to rice for control of rice blast (*Pyricularia oryzae*), to horticultural crops such as apple trees for the control of apple scab (*Venturia inaequalis*), roses for the control of powdery mildew (*Sphaerotheca pannosa*) curcubits for the control of *Botrytis cinerea* and turf for the control of dollar spot (*Sclerotinia homeocarpa*).

Metal complexes of prochloraz are described in our British Pat. No. 1,567,521 and a particularly preferred complex is that formed with manganous chloride in which the molar ratio of prochloraz to manganese is 4:1. However, generally, the prochloraz is present as the free base. The guazatine is generally present as the triacetate salt. The compositions of the invention may be employed in many forms and are often most conveniently prepared in aqueous form immediately prior to use. One method of preparing such a composition is referred to as "tank mixing" in which the fungicidal ingredients in their commercially available form are mixed together by the user in a quantity of water.

In addition to tank mixing immediately prior to use the compositions containing prochloraz and the guazatine fungicides may be formulated into a more concentrated primary composition which is diluted with water or other diluent before use. Such compositions may comprise a surface active agent in addition to the active ingredients and typical examples are a dispersion in an aqueous or non-aqueous vehicle, an emulsifiable concentrate, a dispersible powder or a dusting powder. As a concentrated primary composition the concentration of active ingredients can vary widely and can be for example from 5 to 95 percent by weight of the composition. The primary composition is diluted to give compositions for application to a growing crop in which the amount of active ingredient applied to the crop is as specified below.

An emulsifiable concentrate, also known as a "miscible liquid", comprises a solution of the active ingredients in a non-aqueous solvent in association with one or more emulsifying agents. An emulsion is formed when the emulsifiable concentrate is mixed with water.

A dispersible powder comprises the active ingredients in finely divided form in association with one or more dispersing agents so that a stable aqueous dispersion of the active ingredients is formed on mixing the powder with water. A finely divided inert solid diluent such as kaolin or diatomaceous earth sold under the Registered Trade Mark CELITE is generally incorporated in the dispersible powder.

A dusting powder comprises the active ingredients intimately mixed with a solid pulverant diluent, for example kaolin.

The concentration of the active ingredients (when used as the sole active components) in a composition for direct application to the crop by conventional ground methods is preferably within the range of 0.001 to 10 percent by weight of the composition, especially 0.005 to 5 percent by weight, but more concentrated compositions containing up to 40 percent may be desirable in the case of aerial sprays. When used in treating stored fruit the concentration of the active ingredients is usually in the range of 0.2–1 percent by weight. When treating stored fruit it may also be advantageous to add one or more other active materials which are often used in such circumstances. Examples include 2,4-D (at a concentration of e.g. 0.2–2 percent by weight) and a ripening agent such as ethephon (at a concentration of e.g. 1 to 10 percent by weight).

The invention is illustrated in the following Examples which describe experiments on mixtures of the invention in which a synergistic effect was observed.

EXAMPLE 1

Mature Washington Navel oranges were inoculated at two points on the equator with a benomyl susceptible strain of *Pencillium digitatum* using a small nail which had been dipped in an aqueous suspension of spores of the pathogen. The fruit was then stored for six hours before being dipped with aqueous dispersions of free prochloraz, guazatine triacetate and mixtures of these. The aqueous dispersions were made up by diluting the respective concentrates. The guazatine was the commercially available aqueous concentrate sold under the trade name, Panoctine. The prochloraz concentrate was an emulsifiable concentrate comprising 40% prochloraz and 20% of mixed anionic and non-ionic surfactants dissolved in xylene.

Each treatment was carried out on four groups of twenty oranges. Twenty one days after treatment the oranges were assessed for the number of inoculation points developing lesions. From these data the degree of control of the fungi compared with untreated inoculated oranges can be assessed.

To indicate the existence of synergism between the active components the results were treated in the manner described by Colby S.R. (1967 Calculating Synergistic and Antagonistic Responses of Herbicide Combinations. Weeds 15, 20–22). The values of $E_1$ the expected number of lesions as a percentage of control were calculated from the equation $E_1 = X_1 Y_1/100$ wherein $X_1$ is the number of lesions as a percentage of control with prochloraz at a given concentration when used alone and $Y_1$ is the number of lesions as a percentage of control with guazatine at a given concentration when used alone. If the observed percentage of lesions is less than $E_1$, the results indicate synergism. In Table I below the results with the mixture do show evidence of synergism.

TABLE I

| Concentration of prochloraz (ppm) | Concentration of guazatine (ppm) | Number of lesions/80 oranges* | Lesions as % of control | Expected lesions as % of control ($E_1$) |
|---|---|---|---|---|
| 250 | 0 | 31 | 19.4 | |
| 0 | 250[1] | 105 | 65.6 | |
| 250 | 250[1] | 7 | 4.4 | 12.7 |

*Untreated control group had 160 lesions.
[1]Equivalent to 166 ppm of guazatine base.

EXAMPLE 2

Example 1 was repeated except that Geotrichum candidum was used as the inoculating pathogen and assessment was carried out after 20 days. Synergism was again demonstrated as shown in Table II below.

TABLE II

| Concentration of prochloraz (ppm) | Concentration of guazatine (ppm) | Number of lesions/80 oranges* | Lesions as % of control | Expected lesions as % of control ($E_1$) |
|---|---|---|---|---|
| 250 | 0 | 13 | 31.0 | |
| 0 | 250[1] | 2 | 4.8 | |
| 250 | 250[1] | 0 | 0 | 1.5 |

*Untreated control group had 42 lesions
[1]Equivalent to 166 ppm of guazatine base.

I claim:
1. A fungicidal composition comprising 1-[N-propyl-N-2-(2,4,6-trichlorophenoxy)ethylcarbamoyl]imidazole and bis(8-guanadinooctyl)amine in a ratio of from 2:1 to 1:2 based on the weights of the free bases.
2. The fungicidal composition of claim 1 wherein the imidazole is present as the free base and amine is present as the triacetate salt.

* * * * *